US00PP10000P

United States Patent [19]

Lemon

[11] Patent Number: Plant 10,000

[45] Date of Patent: Aug. 12, 1997

[54] GERANIUM PLANT NAMED 'LOIS'

[75] Inventor: David Lemon, Lompoc, Calif.

[73] Assignee: John Bodger and Sons Company, South El Monte, Calif.

[21] Appl. No.: 571,168

[22] Filed: Dec. 12, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 8,909 9/1994 Walters ..... Plt./87.12

*Primary Examiner*—Howard J. Locker

*Attorney, Agent, or Firm*—Fulwider Patton Lee and Utecht, LLP

[57] ABSTRACT

The cultivar is characterized by its distinctive multi-color presentation. Its strong growth habit and continuous flowering provides for superb cuttings and also for quick recovery following wet weather conditions. The blooms exhibit relatively longer post-harvest production compared to that of other Regal varieties.

1 Drawing Sheet

BACKGROUND OF THE NEW PLANT

The present invention comprises a new and distinct cultivar of *Pelargonium×domesticum* known by the varietal name Lois (Oglevee No. 551, Bodger No. 6 PD 23–3). The new variety was discovered in a selective breeding program by David Lemon at Bodger Seeds, Ltd., Lompoc, Calif. The new variety is a selection from the self-pollenation of Hazel Ripple (unpatented). Hazel Ripple is distinguished from Lois primarily by its smaller flower.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 150–200 parts per million of nitrogen and potassium has a response time of fourteen weeks from the rooted cutting to a flowering plant in a 6.0 inch pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings potted on Nov. 4, 1994 which flowered on Feb. 10, 1995 under full light and greenhouse, and colorings were taken indoors under 200–220 foot candles of fluorescent cool white light using The R.H.S. Colour Chart of The Royal Horticultural Society of London.

THE PLANT

Classification:

*Botanical.*—*Pelargonium×domesticum.*

Form: Upright mound.

*Height.*—23.0–25.0 cm above the media surface.

*Growth.* —Strong; controlled, continuous flowering.

*Strength.*—Free standing; quick rooting.

Foliage: Stalked leaf attachment.

Leaves:

*Size.*—8.0–11.0 cm across; fully expanded leaf.

*Shape.*—Depressed ovate; truncate base.

*Margin.*—Serrately lobed.

*Texture.*—Slightly pubescent; leathery.

*Color.*—Top: Yellow/Green Group 146B; Zone: Not Present. Bottom: Yellow/Green Group 146C.

*Ribs and veins.*—Palmate venation; Color: Yellow/Green group 147C.

Petioles:

*Length.*—4.5–6.5 cm.

*Color.*—Yellow/Green group 146B.

Stem:

*Color.*—Yellow/green group 146C.

*Internodes.*—2.0–3.5 cm in length.

THE BUD

Shape: Elliptical.

Size: 2.5–3.0 cm across; bud just showing color.

INFLORESCENCE

Blooming habit: Continuous blooming; many large florets opening into a full flower head.

Size: 9.0–11.5 cm across.

Borne: Umbel; florets on pedicel; pedicel on peduncle.

Number: About 10 inflorescences per plant.

Florets:

*Closed.*—Bud size: 1.5–2.0 cm in length, 0.5–1.0 cm in width; elliptical; bud showing no color.

*Open.*—Form — Cupped. Color — Top: Outer Edge Red/Purple Group 69D; Upper two petals have a blotch of Red/Purple Group 59A; Upper petal marking is large; Color between margin and marking is RHS 59A; Lower petals: Red/Purple Group 74C with veining of Red/Purple Group 59A; Moderate sized markings of RHS 74C and margin color is RHS 69D; Bottom of petals: Red/Purple Group 69D with veining and blotch showing through faintly; General appearance is bi-color with magenta purple upper petals and light lavender lower petals. Petals — 5–6 in number; single, not united; margin entire. Size — 5.0–6.0 cm across. Texture and appearance — Smooth, satiny; appearance from a distance is a medium purple with dark purple blotch present on upper two petals and dark purple veining present on all petals above medium green foliage.

Petaloids:

*Quantity.*—None.

Pedicel:

*Length.*—2.5–3.0 cm.

Color.—Yellow/Green Group 146B.

Peduncle:

*Length.*—5.0–6.5 cm.

Color.—Yellow/Green Group 146B.

Persistence:

*Disease resistance.*—Not Known.

*Lasting quality.*—Slow to shatter; continuous blooming.

REPRODUCTIVE ORGANS

Stamens:

*Anthers.*—Length: 4.0–5.0 mm.

*Filaments.*—Length: 1.4–1.9 cm; Color: White Group 155D.

*Pollen.*—Golden Brown.

Pistils:

*Number.*—1.

*Length.* —2.2–2.5 cm.

*Stigma.*—5 parted; Color: Red/Purple Group 60C.

*Style.*—Length: 1.4–1.6 cm; Color: Red/Purple Group 60C.

Ovaries: Pubescent; Length: 6.0–7.0 mm; Color: Light Green; superior.

Fruit: None observed.

GENERAL CHARACTERISTICS

Lois adds a new color pattern to the Regal geranium group. The interesting blotching and veining gives Lois' flowers a multi-color presentation. Lois exhibits ease and quickness of rooting, good cutting production, a controlled plant habit, rich medium green foliage and longer post-harvest production, all of which are unique to Lois among Regal geraniums. Given all these positive properties, this variety should please both the grower and the gardener.

I claim:

1. A new and distinct variety of Geranium plant, substantially as shown and described.

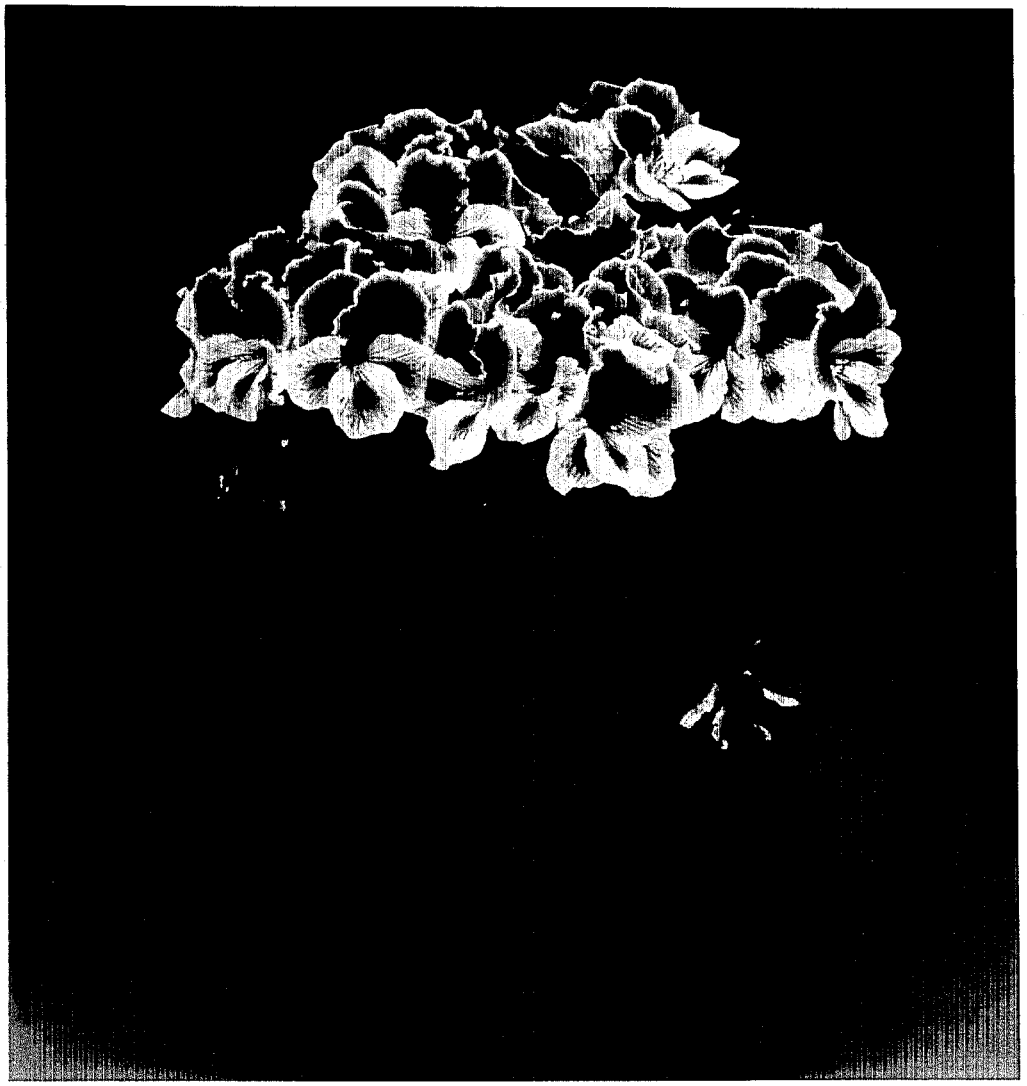

* * * * *